United States Patent
Mulholland

(12)
(10) Patent No.: US 6,464,670 B1
(45) Date of Patent: Oct. 15, 2002

(54) METHOD OF DELIVERING THERAPEUTIC AGENTS TO THE URETHRA AND AN URETHRAL SUPPOSITORY

(75) Inventor: S. Grant Mulholland, Birchrunville, PA (US)

(73) Assignee: BioMed Innovations, LLC, Birchrunville, PA (US)

( * ) Notice: Subject to any disclaimer, the term of this patent is extended or adjusted under 35 U.S.C. 154(b) by 0 days.

(21) Appl. No.: 09/438,563

(22) Filed: Nov. 10, 1999

Related U.S. Application Data

(63) Continuation-in-part of application No. 09/150,423, filed on Sep. 9, 1998, now abandoned.

(51) Int. Cl.[7] .............................. A61K 9/02; A61F 6/06; A61F 13/00
(52) U.S. Cl. .................. 604/288; 424/430; 424/433
(58) Field of Search ......................... 604/11–12, 15, 604/904, 285–288; 424/DIG. 15, 426, 428, 430, 431, 433, 436

(56) References Cited

U.S. PATENT DOCUMENTS

| | | | |
|---|---|---|---|
| 183,388 A | 5/1876 | Fowler | |
| 246,697 A | 9/1881 | Wadleigh | |
| 1,218,478 A | 3/1917 | Sappington | |
| 1,737,949 A | 12/1929 | Schaaf | |
| 1,767,785 A | 6/1930 | Sushko | |
| 2,123,750 A | * 7/1938 | Schulz | 604/904 |
| 2,877,767 A | * 3/1959 | Kramer | 604/11 |
| 3,032,036 A | * 5/1962 | Rader et al. | 604/11 |
| 3,126,887 A | 3/1964 | Gordon | |
| 3,689,514 A | 9/1972 | Neissner | |
| 3,690,321 A | * 9/1972 | Hirschman | 604/11 |
| 3,817,248 A | 6/1974 | Buckles et al. | |
| 3,840,010 A | 10/1974 | Giglio | |
| 3,905,372 A | * 9/1975 | Denkinger | 604/904 |
| 4,317,447 A | 3/1982 | Williams | |
| 4,551,148 A | 11/1985 | Riley et al. | |
| 4,678,466 A | 7/1987 | Rosenwald | |
| 4,911,687 A | * 3/1990 | Stewart et al. | 604/15 |
| 5,002,540 A | 3/1991 | Brodman et al. | |
| 5,085,650 A | 2/1992 | Giglio | |
| 5,176,907 A | 1/1993 | Leong | |
| 5,336,163 A | * 8/1994 | DeMane et al. | 604/11 |
| 5,479,945 A | 1/1996 | Simon | |
| 5,766,145 A | * 6/1998 | Fox et al. | 604/15 |
| 5,891,081 A | * 4/1999 | McNelis et al. | 604/14 |

\* cited by examiner

Primary Examiner—Dennis Ruhl
(74) Attorney, Agent, or Firm—Drinker Biddle & Reath LLP

(57) ABSTRACT

A urethral suppository having a shaft shaped for cooperating with the action of the periurethral musculature to retain the suppository within the urethra, and having a knob extending from an end of the shaft sized to prevent over insertion of the suppository. A method of delivering one or more therapeutic agents to the urethra and associated structures, the method involving insertion of the urethral suppository into the urethra.

21 Claims, 3 Drawing Sheets

METHOD OF DELIVERING THERAPEUTIC AGENTS TO THE URETHRA AND AN URETHRAL SUPPOSITORY

This application is a continuation-in-part application of U.S. Application Ser. No. 09/150,423 filed on Sep. 9, 1998, now abandoned.

FIELD OF THE INVENTION

This invention relates to a method of delivering therapeutic agents to the urethra, bladder and related structures and an urethral suppository for use in delivering therapeutic agents thereto.

In the treatment of various ailments affecting the urethra, bladder and related structures, it is generally not desirable to deliver therapeutic agents systemically. When delivery of such agents is accomplished in a systemic fashion such as, for example, orally or by way of a remote intravenous, intramuscular, subcutaneous or transdermal route, relatively high dosages are required in order to deliver an amount to the affected areas sufficient to have the desired therapeutic effect. The requirement for such relatively high dosages results from the dilution and dissipation effects attendant to such delivery methods as well as the loss of efficacy that can result from biochemical interactions between the therapeutic agent and unrelated systems. Further, due to the relatively high dosages required by systemic delivery methods, the risks of triggering both adverse reactions and unwanted side effects are increased. Accordingly, it is known to employ delivery methods which provide for the local application of therapeutic agents in the treatment of urethral, bladder and related ailments in order to administer relatively small dosages to achieve delivery of relatively high concentrations of such agents to the affected areas.

While the local application of therapeutic agents permits the use of smaller dosages, and can avoid certain of the drawbacks associated with systemic delivery methods as mentioned herein above, a different set of problems arise with respect thereto. In the context of treating conditions affecting the urethra, bladder and related structures, for example, it is of primary importance that the local application of therapeutic agents be accomplished in a manner compatible with the anatomical structures involved. Accordingly, it is known to employ suppositories as delivery devices for therapeutic agents. Such suppositories are designed to be inserted into the urethra and to release therapeutic agents contained therein or applied thereon to the mucosal lining of the urethra. The release of therapeutic agents occurs upon liquefaction of the suppository which results from the transfer to the suppository of the body heat of the patient into whose urethra the suppository has been placed (Amemiya, T.; et. al. Development of emulsion type new vehicle for soft gelatin capsule. I. Selection of surfactants for development of new vehicle and its physical chemical properties. Chemical and Pharmaceutical Bulletin, 1998, Feb, 46(2): 309–13).

Various prior art suppositories, however, have been designed in such a manner that they are difficult to retain in position within the urethra where the precise delivery of therapeutic agents is desired. Experience has shown that such suppositories tend either to advance inwardly into the bladder or to be expelled out of the urethra prior to the complete decomposition within the urethra. In either case, the desired result of a precise placement of the specific dosage of the selected therapeutic agents within the urethra is not realized.

In order to address these shortcomings, it is known to configure urethral suppositories in the form disclosed in U.S. Pat. No. 5,085,650 to Giglio (the '650 patent). The '650 patent discloses an urethral suppository comprising a bulbous head and a conical tail joined by a narrow cylindrical shaft. As taught by the '650 patent, upon insertion of the suppository into the urethra of a human female patient, the bulbous head thereof is advanced through the entire length of the urethra and penetrates into the bladder to anchor the suppository at the bladder neck. The conical tail of the suppository prevents the further advance of the suppository into the bladder. More specifically, once the suppository is positioned within the urethra, the portion of the bulbous head of the suppository which curves inwardly toward the shaft is designed to prevent the suppository from expulsion by its contact with the bladder walls at the bladder neck where the bladder narrows to the meet the proximal end of the urethra. At the same time, the flared portion of the conical tail, having an increasingly larger diameter than the shaft of the suppository as well as the urethra itself, is designed to prevent the suppository from over insertion by contact with the edges of the urethral orifice at the distal end thereof. It is through this combination of contact surfaces that the suppository disclosed in the '650 patent is intended to be held in position during the liquefaction thereof While suppositories configured with bulbous heads, conical tails and narrow cylindrical shafts, as disclosed in the '650 patent aid in the placement and retention of suppositories within the urethra as compared with purely cylindrical suppositories that lack such features, such configurations permit, nonetheless, some slippage and, moreover. present certain other disadvantages. Because retention of the suppository is effected, in part, by the contact between the inwardly curved portion of the bulbous head with the bladder neck, it is required that the bulbous head of the suppository advance beyond the urethra and invade into the bladder itself. As a result, where therapeutic agents are infused throughout the material comprising the suppository, the portion of the dosage contained within the material comprising the bulbous head thereof is not positioned so that it is in direct physical contact with the mucosal lining of the urethra and thus is not absorbed readily therein. As a result, the precise delivery of a specific dosage through absorption by the urethra cannot be realized effectively. Further, insofar as the conical tail section of the suppository disclosed in the '650 patent has a flat base, it is difficult to manipulate after insertion as it provides no projections which can be grasped readily. Moreover, the roundness of the conical tail renders the distal end of the suppository less than fully compatible with the anatomical structure of the labia. As a result, the comfort of the patient is compromised.

Any foreign body inserted into the urethra or bladder causes a degree of urgency, frequency, pain, and general discomfort to the patient. Medical devices, such as tubes, catheters, or instruments, commonly inserted in the bladder or urethra during urological procedures cause discomfort to patients (Duckett, J W; et. al. Intravesical morphine analgesia after bladder surgery. Journal of Urology, 1997, Apr 157(4): 1407–9;Campbell's Urology. Edited by Walsh, P C; et. al. W. B. Saunders and Company, Six Edition, 1992). This discomfort can become extreme when the device contacts the sensitive tissue of the bladder neck. As an example, Foley catheters are used to provide bladder drainage after surgery when normal voiding is compromised. Foley catheters are tubes inserted through the urethra into the bladder. Inflation of a balloon at the catheter tip aids in the retention of the catheter in the bladder, but causes extreme discomfort to the patient as a result of contact between the balloon and the bladder neck. The patient feels urgency and a burning sensation that persists for a period of up to 24 hours. Typically, these patients are given local anesthetics such xylocaine to reduce the discomfort during this initial period.

The bladder neck is a highly vascularized and innervated tissue containing specialized cells that play an important role in the voiding cycle. The bladder is very sensitive to pressure. Any foreign body within the bladder neck will cause major discomfort to the patient. Various prior art suppositories have been designed which do not take into consideration the effect of contacting the bladder neck with a portion of the suppository. In addition, when portions of the suppository reside in different tissues such as the bladder neck and urethra, the dose of drug delivered by the suppository to an afflicted tissue cannot be readily determined. This is a result of different tissues causing the suppository to liquefy at different rates and having different rates of drug absorption.

The present invention relates to the provision of an improved method for delivering a therapeutic agent to the urethra and an easily manipulatable urethral suppository which is designed to overcome disadvantages associated with prior art suppositories.

Accordingly, an object of the present invention involves provision of a suppository shaped for cooperating with the action of the periurethral musculature to retain the suppository within the urethra with a minimum of pain and discomfort to the patient. Another object involves providing a suppository in which no portion of the suppository extends outside the urethra into the bladder, and does not make contact with the highly sensitive tissue of the bladder neck or urethral sphincter. A further object involves providing a one-size suppository which fits all patients regardless of their urethral length, and which remains stationary in the urethra regardless of body motion.

SUMMARY OF THE INVENTION

In accordance with one aspect of the present invention, there is provided a method for delivering a therapeutic agent to the urethra, bladder and related structures comprising the steps of providing a suppository comprising one or more therapeutic agents and a biocompatible carrier medium and shaped to be capable of cooperating with the action of the periurethral musculature and surrounding organs to retain the suppository within the urethra, inserting the suppository into the urethra, and retaining the suppository within the urethra by the action of the periurethral musculature for a period of time sufficient to permit the therapeutic agent to diffuse substantially into the urethra, in particular, the bladder and the vagina. The suppository utilized in the method of the present invention may be of any shape capable of being inserted into the human female urethra and of cooperating with the periurethral musculature in retaining the suppository within the urethra.

In accordance with another aspect of the present invention, there is provided an urethral suppository shaped to be capable of cooperating with the action of the periurethral musculature to retain the suppository within the urethra. Preferably, the suppository comprises a shaft having a rounded first end tapering along a longitudinal axis to a second end, and a substantially ellipsoidal knob extending from the second end of the shaft and sized to prevent insertion into the urethra, said shaft and knob comprising a composition of at least one therapeutic agent and a biocompatible carrier medium. More preferably, ellipsoidal knob of the suppository has a major axis which is substantially perpendicular to the longitudinal axis of the shaft. It is also preferred that the biocompatible carrier medium is capable of forming a relatively soft, pliable and smooth suppository so that the need for a lubricant to aid insertion can be eliminated and the risk of patient discomfort can be minimized.

The tapered shaft of the preferred suppository of the present invention provides a profile to the suppository which is particularly well suited to work in concert with the normal-action of the periurethral musculature, the urethral wall and surrounding organs found in human females. So configured, the naturally occurring pressure exerted by the periurethral musculature, the tissues of the urethral wall and surrounding organs is most advantageously utilized in retaining the suppository entirely within the urethra without contacting the tissue of the bladder. This retention permits the complete delivery of a precise dosage of one or more therapeutic agents to the mucosal lining of the urethra thereof without invasion into the bladder and which does not prevent the therapeutic agent within the liquified carrier agent from flowing into the bladder, vagina or related organs.

DETAILED DESCRIPTION OF THE INVENTION

Figure 1:
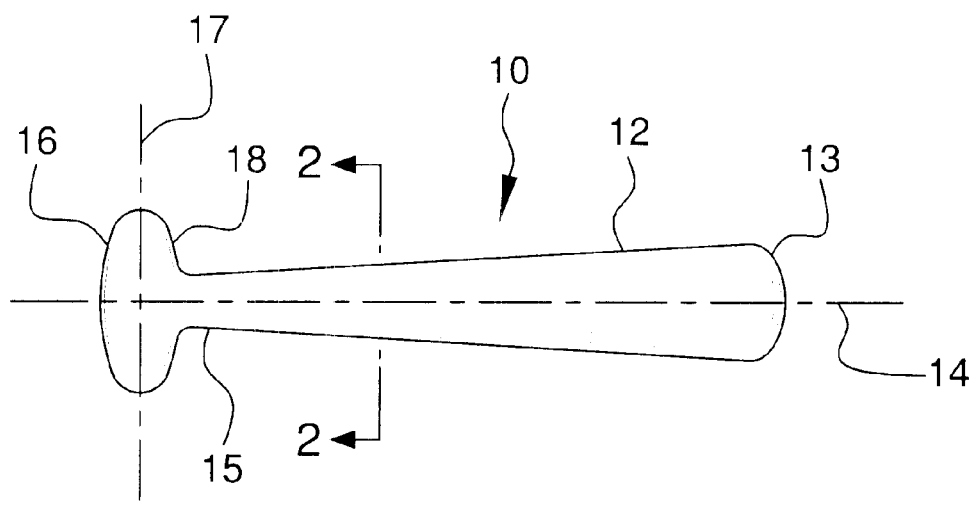
FIG. 1 shows a profile view of a preferred suppository of the present invention.

The urethra of the adult human female is a substantially tubular structure which serves as the outlet for urine from the bladder. While the urethra of the adult human female has some degree of variation in size across any given population, it is generally about 3 to about 4 centimeters in length and about 0.8 to about 1.5 centimeters in diameter upon full expansion. The flow of urine from bladder is controlled by certain muscles which surround the urethra and exert forces inwardly to constrict the urethra. The flow of urine from the bladder is a complicated process controlled by the interaction of a host of specialized tissues and pathways. In the female, a thin layer of smooth muscle extends along the entire length of the urethra playing an important role in maintaining continence. A band of striated muscle around the distal urethra forms the distal sphincter. The striated pelvic floor muscle is external to this distal external sphincter. During the filling and voiding cycles in women, the interaction of these muscles, in addition to changes in position of the urethra and bladder neck, control the flow of urine. Thus, continence in women is a process that is effected by both the active and passive forces generated by the tissues of the urethra, bladder, and surrounding organs. It will be understood that as used herein the muscles which surround and impinge upon the urethra will be referred to herein collectively as the periurethral musculature.

The forces applied by the periurethral musculature, however, are not exerted evenly along the length of the urethra. Rather, due to the physical arrangement of the periurethral musculature with respect to the urethra due to the anatomy, orientation, and activation of the periurethral musculature, these forces are applied differentially. Considering an average adult human female urethra of about 4 centimeters in 1 centimeter intervals beginning at the bladder, the forces exerted by the periurethral musculature increase substantially from the first to the second centimeter, increase further to a maximum within the third centimeter, and drop off significantly in the last centimeter. Examining the pressure within the urethra in one centimeter intervals beginning at the bladder neck or proximal portion of the urethra, the forces exerted by the periurethral musculature create a substantially increasing pressure from the first to the second centimeter. The pressure continues to increase from the second centimeter reaching a maximum within the third centimeter. The pressure then drops off significantly in the last centimeter. This profile of urethral pressures is substantially the same from patient to patient as it is a direct consequence of the anatomical configuration and location of the human female periurethral musculature, i.e. the anatomy, orientation, and activation of the human female periurethral musculature.

In view of this specific pressure profile, a key feature which serves to retain the suppositories disclosed in the '650 patent within the urethra, namely the inwardly curving portion of the bulbous head, is designed to do so at a region of low urethral pressure. In contrast, the present invention takes advantage of the naturally occurring forces exerted by the periurethral musculature in holding the suppository in place. It is designed specifically to work in concert with the distinctive pressure profile of the human female periurethral musculature. As a result, slippage of the present suppository within the urethra is minimized and precise delivery of the therapeutic agent thereto is achieved.

The forces generated within the urethral wall act perpendicular to the surface of any object in the urethral lumen. Therefore, the force profile acting on the surface of the cylindrical portion of the '650 suppository, parallel to the axis of the urethra, is essentially equivalent to the pressure profile generated by the force in the urethral wall described above. Movement of the '650 suppository in the urethra is constrained by the shape of the bulbous head and conical tail. The larger diameter of these sections prevents the '650 suppository from lateral movement out of the urethra or into the bladder. Movement of the suppository in either direction in the urethra is undesirable, as the medication will be removed from contact with the urethral wall and not provide the desired therapeutic benefit.

However, the bulbous head of the '650 suppository resting in the bladder neck is not a desirable feature for a urethral suppository. The presence of an object lying in the bladder neck of a patient can be very irritating causing discomfort, pain, urgency and frequency as described above. In contrast, the present invention takes advantage of the naturally occurring forces within the urethral wall, particularly those exerted by the periurethral musculature, to hold the suppository in place. The suppository of the present invention is designed specifically to work in concert with the distinctive pressure profile generated within the urethral lumen of the human female by the periurethral musculature. As a result, movement of the suppository of the present invention within the urethra is minimized, irritation to the bladder neck is avoided, and a controlled and measurable delivery of the therapeutic agent thereto is achieved.

The provision of a suitably shaped suppository is important to the practice of the method of the present invention.

While the suppository utilized in the method of the present invention may be provided in any of a variety of shapes which are capable of insertion into the human female urethra, it is important that the shape of the suppository also be such that it is capable of cooperating with the pressure profile, i.e. the force generated within the urethral wall by the periurethral musculature and other tissue elements of the human female periurethral musculature to secure the suppository within the urethra. More specifically, and as described more fully herein above, the periurethral musculature exerts inward forces upon the urethra in a differential manner with the greatest inward forces being located at a region approximately three centimeters distal to the bladder in the distal third of the urethra from the bladder. Accordingly, it is important that the suppository provided in the method of the present invention have a shape which, upon insertion into the urethra, cooperates with these forces and permits the region of greatest urethral pressure to impinge thereon in a manner which promotes the secure placement and retention of the suppository within the urethra while causing the least amount of irritation and discomfort to the patient. In a preferred embodiment of the method of the present invention, the suppository provided will be of a shape as shown substantially in FIGS. 1–3.

The therapeutic agents suitable for use in the suppository provided in the method of the present invention may be any of a wide variety of compounds, substances, pharmaceuticals,, and the like which are capable of being absorbed through the mucosal lining of the human female urethra, either alone or in combination with biocompatible absorption aids, and which have been approved or which will be approved for the diagnosis, treatment, prophylaxis, cure or mitigation of any disease of the urethra, bladder or associated structures. Such therapeutic agents include, without limitation, antibiotics, antimicrobials, antifungal agents, analgesics, steroidal and non-steroidal anti-inflammatory agents, hormones such as estrogen and progesterone, mucous production stimulators such as pentosan polysulfate sold under the trademark Elmiron(brand) by Alza Corporation, anti-spasmodics such as oxybutynin chloride sold under the trademark Ditropan by Hoechst Marion Roussel, Inc., and the like. The urethral suppositories employed in the method of the present invention are particularly well suited to the treatment of various infections, incontinence, uninhibited neurogenic or reflex neurogenic bladder (i.e., urgency, frequency, urinary leakage, urge incontinence, dysuria), and non-specific urethritis as well as post-menopausal urethral and bladder symptoms (Winkler, H A, and Sand, P K. Treatment of detrusor instability with oxybutynin rectal suppositories. International Urogynecology Journal and Pelvic Floor Dysfunction, 1998, 9(2): 100–2).

The therapeutic agents suitable for use in the suppository provided in the method of the present invention may also comprise compounds or substances used in conjunction with medical procedures such as catheterization, cystoscopy or transurethral surgery. Such therapeutic agents include, for example, antimicrobials, steroidal and non-steroidal anti-inflammatory agents, and topical anaesthetics such as lidocaine, procaine, benzocaine, xylocaine and the like.

The biocompatible carrier medium suitable for use in the suppository employed in the method of the present invention may be selected from any of a wide variety of biocompatible materials which are capable of being combined with the desired therapeutic agents. With respect to the physical characteristics of the biocompatible carrier media, it is important that such media are capable of becoming sufficiently rigid at room temperature to be inserted into the human female urethra and of liquefying within a relatively short period of time upon insertion therein. Preferably, the biocompatible carrier medium is capable of being formed into relatively soft, pliable and smooth suppository so that comfort of the patient and ease of use is optimized. In certain preferred embodiments, the biocompatible carrier medium is also self-lubricating, water-soluble, substantially non-staining and substantially free of parabens.

Biocompatible carrier media suitable for use in the suppository provided in the method of the present invention include a wide variety of polymers which are soluble in body fluids such as, for example, vegetable gums such as carrageenan, modified celluloses such as hydroxypropylcellulose or hydroxypropylmethylcellulose, polyvinyl alcohol, polyvinylpyrrolidone, polyacrylamide, polyethylene glycol, poly(phosphoester-urethanes), ethylenoxide polymers, and the like. Preferably, the biocompatible carrier medium is selected so that the entire mass thereof is completely liquified within the urethra within about ten minutes, and even more preferably within about five minutes. However, in any case, the biocompatible carrier medium is selected so as to completely liquify within the urethra within a period of time that optimizes the delivery of the therapeutic agent. This may range from five to ten minutes for analgesics, for example, or up to two hours or longer for anticholinergic agents.

The concentration of therapeutic agents found in the suppository employed in the method of the present invention will vary in accordance with, among other things, the nature of the therapeutic agents, their physiologic role, the desired therapeutic effect, and the manner in which the therapeutic agents and the biocompatible carrier medium are combined. Thus, for example, the concentration of female hormones, such as estrogen or progesterone, will likely be different from the concentration of an anaesthetic or dilator used in connection with the performance of a medical procedure (Waring, S C; et. al. Postmenopausal estrogen replacement therapy and risk of AD: a population-based study. Neurology, 1999, Mar 23, 52(5): 965–70).

The insertion step of the method of the present invention may be accomplished by any means suitable for effecting the placement of the suppository within the urethra. Such means may include, for example, manual or instrument-assisted insertion either by a health care professional or the patient herself. The suppository is placed in the urethra for a sufficient period of time for the therapeutic agent to diffuse from the suppository to a chosen target tissue, e.g. urethra, bladder, vagina and related tissues. It is understood that the term "diffuse" refers to any physical chemical movement of the therapeutic agent from the suppository to the tissues of interest whereby the therapeutic agent otherwise traverses from the suppository to contact at least the luminal wall of the urethra.

The urethral suppository of the present invention comprises a therapeutic agent and a biocompatible carrier medium which are combined and formed into a shape suitable for insertion into the human female urethra and capable of cooperating with the action of the periurethral musculature to retain the suppository within the urethra. While the therapeutic agent or agents as well as the biocompatible carrier medium may be selected from any of a wide variety of materials appropriate for inclusion in an urethral suppository as set forth more fully herein above, it is important that the urethral suppository of the present invention have certain shape characteristics. It is by means of these shape characteristics that the urethral suppository of the present invention advantageously utilizes the action of the periurethral musculature in securing the position of the suppository within the urethra, provides for ease of insertion and manipulation, and promotes the comfort of the patient through compatibility with the external structures of the human female genital anatomy.

Figure 2:
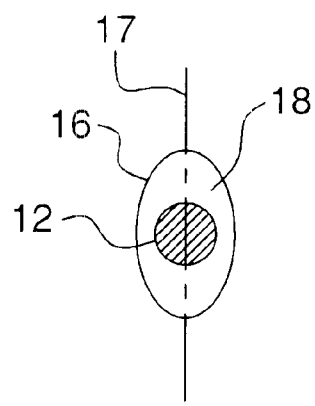
FIG. 2 shows a cross-sectional view of a preferred suppository of the present invention as shown from line 2—2 of FIG. 1.

In accordance with a preferred embodiment of the present invention, and with reference to FIG. 1, the suppository 10 comprises a shaft 12 having a rounded first end 13 tapering along a longitudinal axis 14 to a second end 15 and a substantially ellipsoidal knob 16 sized to prevent insertion into the urethra which extends from the second end 15 which has a major axis 17 wherein the major axis 17 of the knob 16 is substantially perpendicular to the longitudinal axis 14 of the shaft 12. As shown in FIG. 2, the shaft 12 is substantially circular. It is by means of the tapering of the shaft 12 that retention substantially entirely within the urethra by cooperation with the periurethral musculature and other tissue elements within the urethral wall is advantageously realized. More specifically, upon insertion of the suppository into the urethra, the first end 13 (where the diameter of the shaft 12 is at its greatest) corresponds to the proximal end of the urethra (where the urethra meets the bladder) at which the force of the periurethral musculature is the lowest. As the force exerted by the periurethral musculature increases from a minimum at the proximal end of the urethra to a maximum at about three centimeters distal thereto, the diameter of the shaft 12 decreases. The tapering of the shaft 12 continues to the second end 15 at which a substantially ellipsoidal knob 16 extends substantially perpendicular to the longitudinal axis 14 of the shaft 12 thereby preventing overinsertion thereof.

As a result of this configuration, the region of strongest urethral pressure contributes substantially to the retention of the suppository within the urethra. In order for the suppository to be withdrawn, the force applied to the suppository must overcome the incrementally increasing resistance offered by the region of greatest urethral pressure on the increasing diameter of the shaft 12. This interplay between the region of greatest is urethral pressure and narrowest shaft diameter yields a significant improvement over urethral suppositories found in the prior art with respect to the retention of the suppository within the urethra and comfort to the patient. Accordingly, the precise delivery of therapeutic agents to and absorption by the mucosal lining of the urethra is advantageously achieved and patient tolerability of the suppository is enhanced.

The movement of the suppository caused by forces in the urethral wall acting on the surface of the suppository is governed by the geometry of the suppository and the distribution of the forces across the surface of the suppository. In the simplest case, a perfectly cylindrical suppository extending outside either end of the urethra (thereby eliminating end conditions) will have a distribution of radial forces acting on the surface of the cylindrical suppository. The radial distribution results from the force within the urethral wall acting perpendicular to the surface of the suppository, parallel to the axis of the urethra. The magnitude of the radial distribution of forces acting on the suppository will be the same as the pressure profile within the urethral wall described above for the periurethral musculature. However, in reality, the forces in the urethral wall are not purely radial, but include lateral components contributed by the peristaltic motion of the urethra and other structural and functional elements. These lateral forces must be balanced if an object is to remain stationary in the urethra.

A suppository may only remain stationary in the urethra if all lateral forces acting on the suppository are balanced. In the present invention, the ellipsoidal head, 16, prevents the suppository, 10, from moving in the direction of the bladder. Lateral forces acting on the suppository, 10, in the bladder direction are balanced by forces acting against the elliptical head, 16, in the urethral orifice. In this fashion, the ellipsoidal head serves the same function as the conical tail of the '650 suppository, but in manner that is more physiologic to the structure of the surrounding tissues.

Lateral forces acting in to expel the suppository from the body must also be balanced to maintain a suppository in the urethra. Forces acting to expel the '650 suppository are balanced by forces acting in the bladder neck against the bulbous head. However, contact of the bladder neck with the bulbous head causes severe discomfort to the patient. The present invention also balances the forces acting to expel the suppository from the body. However, the present invention achieves this goal without contacting the bladder neck significantly reducing discomfort to the patient. This balance of forces is achieved by shaping the suppository so a component of the force acts in the direction of the bladder. In this fashion, the suppository is prevented from being prematurely expelled out the urethra and from the body.

Figure 3:
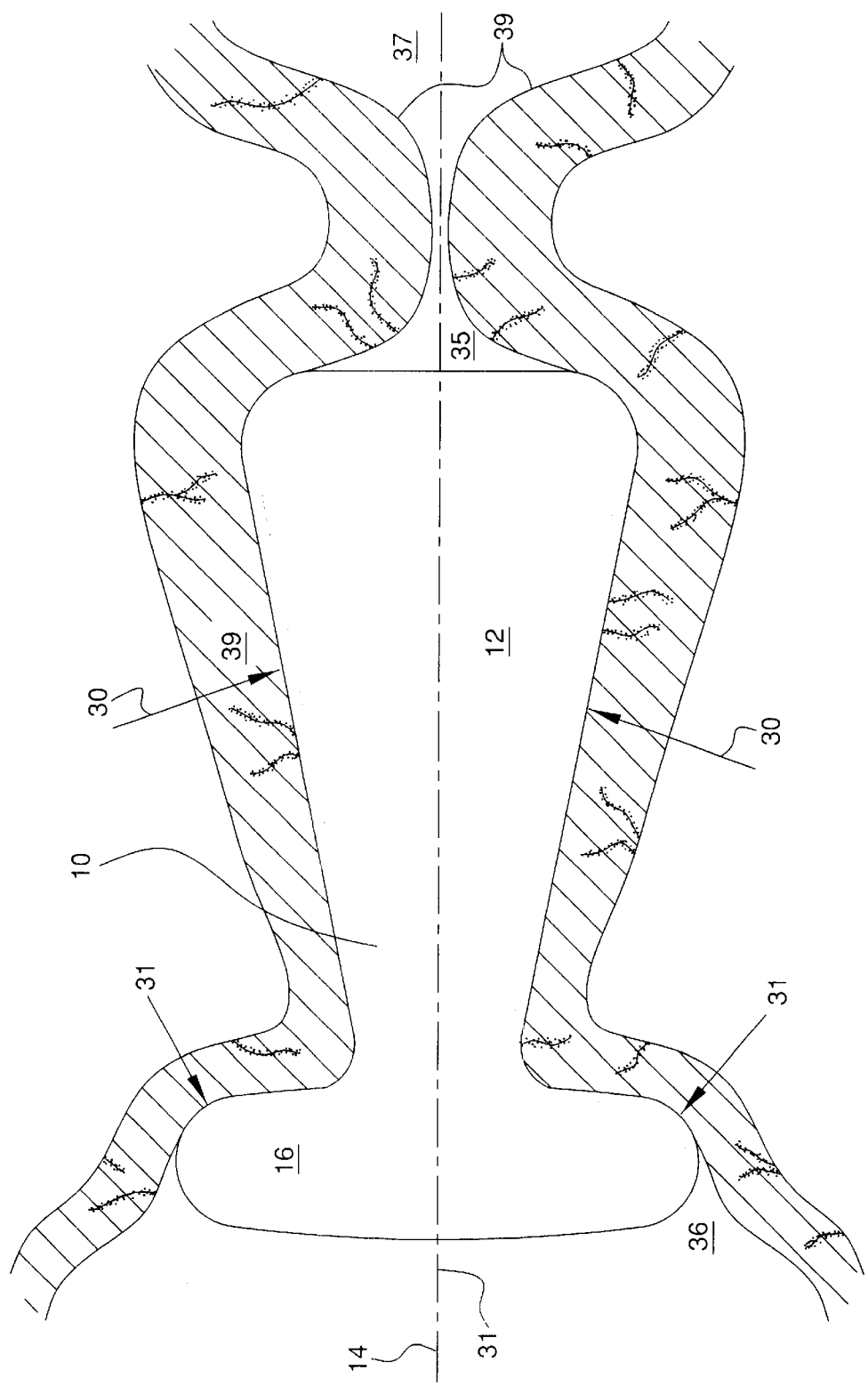
FIG. 3 shows a profile of a preferred suppository of the present invention inserted in the urethra.

In accordance with a preferred embodiment of the present invention, and with reference to FIG. 3, the suppository, 10, is shown in a female urethra, 35. The ellipsoidal head, 16, is positioned in the urethral orifice, 36. The force, 31, acting against the ellipsoidal head, 16, in the urethral orifice, 36, prevents the suppository, 10, from moving into the bladder, 37. The force, 31, represents the sum of all forces acting against the ellipsoidal head, 16, in the urethral orifice, 36. The shaft, 12, of the suppository, 10, is completely in the lumen of the urethra, 35, and does not protrude into the bladder, 37. The longitudinal axis, 14, of the shaft, 12, parallels the longitudinal axis, 50, of the urethra, 35. The shaft has a variable diameter profile along said length, the diameter being inversely proportional to the magnitude of force generated within the urethral wall by the periurethral musculature. The force, 30, generated within the urethral wall, 39, acts perpendicular to the surface of the suppository, 10. The force, 30, represents the sum of all forces generated within the urethral wall, 39, in contact with the suppository, 10. This force prevents the suppository, 10, from being expelled from the urethra, 35.

Figure 4:
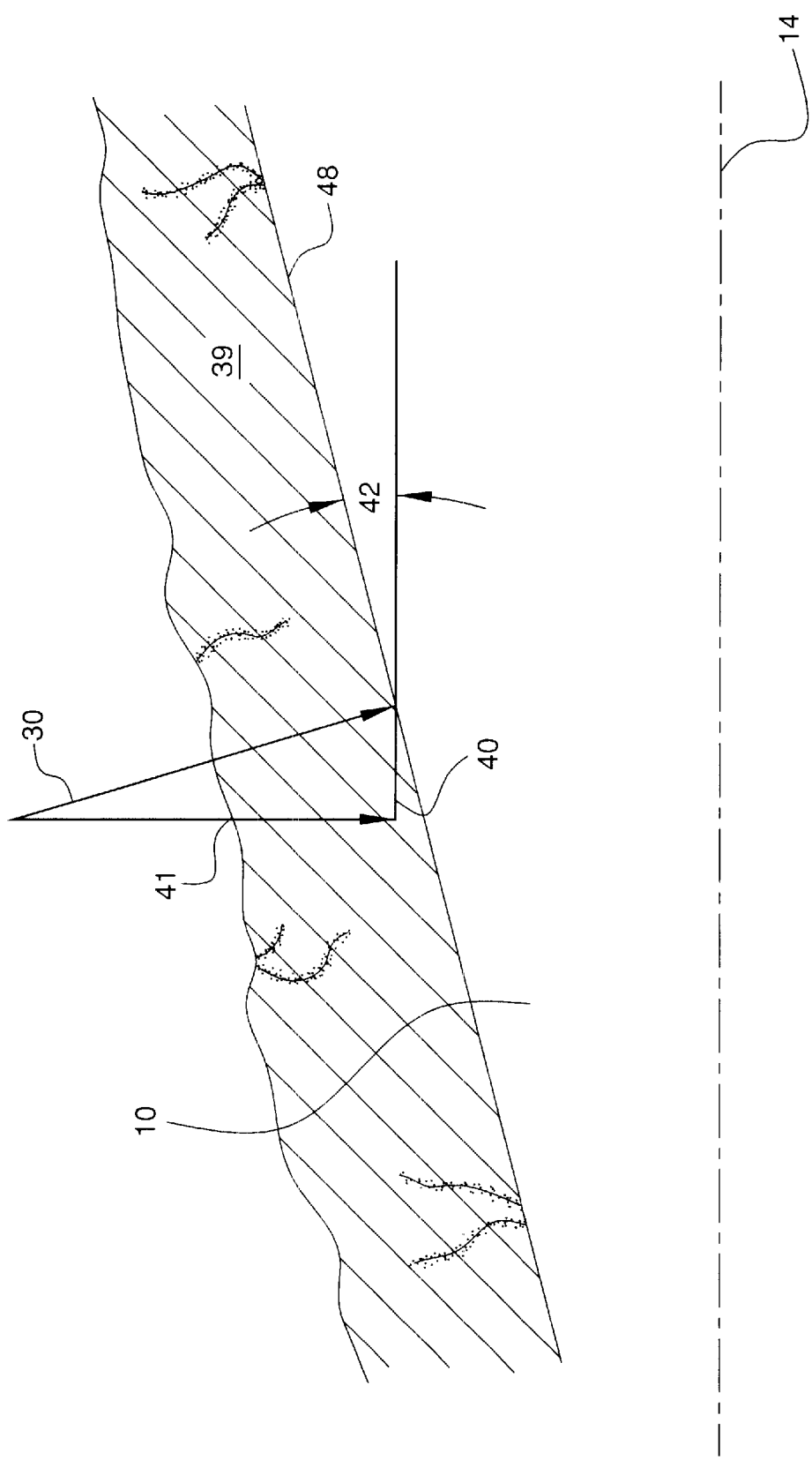
FIG. 4 shows a section of the suppository inserted in the urethra, forces exerted on the suppository by the urethral tissues, and the shape of the suppository which, in combination with the forces exerted by the urethral wall on the suppository, wedges the suppository in place.

The force, 30, shown in detail in FIG. 4, has two components, a lateral component, 40, and a radial component, 41. The radial component, 41, of the force, 30, is balanced by the symmetry of the suppository, 10, within the lumen of the urethra, 35. The lateral component, 40, acting on the surface of the suppository, 10, works to oppose the forces acting to expel the suppository, 10, from the urethra, 35. The magnitude of the lateral component, 40, of the force, 30, acting on the suppository, 10, is determined by the angle, 42, between the surface of the suppository, 48, and the longitudinal axis, 14, of the shaft, 12, and the magnitude of the force, 30, generated in the urethral wall, 39.

The balance of forces acting on the suppository, 10, determines the movement of the suppository, 10, in the urethra, 35. The angle, 42, determines the magnitude of the force working the distal movement of the suppository, 10, out of the urethra, 35. As the angle, 42, increases, the lateral force, 40, working in the direction of the bladder, 37, increases. The ellipsoidal head, 16, resting in the urethral orifice, 36, provides a balance to the lateral force, 40, acting to move the suppository towards the bladder. Increasing the angle, 42, increases the lateral force, 40, causing the ellipsoidal head, 16, to press harder against the urethral orifice, 36. In this manner, the suppository, 10, remains in the urethra without the need to contact the sensitive tissue of the bladder neck, 39. The urethral suppository of claim 13 wherein said profile is sufficiently shaped to render a lateral component of urethral luminal force acting at a point on a surface of said suppository in contact with said lumen at said point of luminal force sufficient to oppose forces acting to expel said suppository from said urethra.

The shaft profile or length profile, which has a tapering diameter, is sufficiently shaped to render a lateral component of the urethral luminal force acting at a point on a surface of the suppository in contact with the lumen at that point of luminal force sufficient to oppose forces acting to expel said suppository from the urethra.

Additionally, the balance of the lateral force, 40, with the action of the ellipsoidal head, 16, against the urethral orifice, 38, prevents movement of the suppository, 10, irrespective of body motion or urethral length. This allows one size of suppository to fit all patients.

The ellipsoidal knob 16 also contributes to the anchoring of the suppository within the urethra. Insofar as the major axis 17 of the knob 16 extends substantially perpendicularly to the longitudinal axis 14 of the shaft 12, and is sized to prevent insertion into the urethra, the knob 16 serves to prevent the advance of the suppository into the bladder. More specifically, the inwardly curved face surface 18 of the knob 16 which extends circumferentially about the second end 15 of the shaft 12, as shown in FIG. 2, prevents over insertion of the suppository by its contact with the urethral orifice (not shown). Moreover, due to its ellipsoidal shape, the knob 16 is easily palpable by the person performing the insertion. If subsequent manipulation is required, either to effect repositioning or early withdrawal, the knob 16 provides means for grasping the suppository readily. Finally, as a result of the substantially ellipsoidal shape of the knob 16, the suppository is compatible with the external anatomy of the human female. More specifically, the ellipsoidal nature of the knob 16 permits the alignment of the major axis 17 with the contours of the labia minora of the patient so as to afford greater comfort in the use of the suppository.

It will be understood that the dimensions of the various portions of the suppository of the present invention are important to the successful practice of the invention. That is, the suppository must be of such a size that it is properly retainable within the urethra while not being so large as to cause undue discomfort to the patient during insertion and use. Within such bounds, however, and depending on the particular dimensions of the urethra into which the suppository will be inserted, variations in the dimensions of the various portions of the suppository may occur.

In certain preferred embodiments it has been found that the shaft of the suppository will have a longitudinal axial length of about 3.5 to about 5 centimeters, preferably about 4 to about 4.5 centimeters, a diameter at the first end thereof of about 0.8 to about 1. 5 centimeters, preferably about 0.8 to about 1.2 centimeters, and a diameter at the second end thereof of about 0.4 to about 1 centimeters, preferably about 0.5 to about 0.7 centimeters. In such preferred embodiments, the ellipsoidal knob will have a major axis of about 1 to about 2 centimeters, preferably about 1.3 to about 1.7 centimeters.

With respect to the manner in which the therapeutic agents and the biocompatible carrier medium are combined in the suppository of the present invention, the therapeutic agent loading level for a given suppository will vary in accordance with, among other things, whether such therapeutic agent is chemically bound to the selected biocompatible carrier medium, is physically mixed therewith prior to formation into a suppository, or coated on the surface thereof after formation into a suppository or combinations thereof For those embodiments in which the therapeutic agent is chemically bound to the selected biocompatible carrier medium, the concentration of the therapeutic agent can be as high as the stoichiometric ratio of one therapeutic agent molecule per biocompatible carrier medium bonding site (Novel Drug Delivery. edited by Prescott and Nimmo, Wiley and Sons, 1989).

For those embodiments in which the therapeutic agent is physically mixed with the selected biocompatible carrier medium prior to formation into an urethral suppository or applied as a coating on a preformed urethral suppository, the concentration of the therapeutic agent will vary in accordance with the particular agents that are employed and the application for which the suppository is used. In certain embodiments, the therapeutic agent will be applied differentially to the surface of the biocompatible carrier medium. More specifically, in embodiments in which the therapeutic agent forms a coating on the surface of the biocompatible carrier medium which has already been formed into a suppository, the concentration of the therapeutic agent will vary along the length thereof. In this manner, the precise delivery of different amounts of a therapeutic agent to different portions of the urethra may be realized. In any event, the desired amount of a particular therapeutic agent to be used, and the preferred manner in which the therapeutic agent is combined with the selected carrier medium will be readily ascertainable by one of ordinary skill in the art for each particular application.

What is claimed is:

1. A urethral suppository formed from meltable biocompatible material, said suppository comprising:
    (a) a shaft having a first end and tapering toward a second end; and
    (b) a knob extending from the second end of said shaft and sized to prevent insertion of said knob into the urethra,
    wherein said suppository comprises at least one therapeutic agent.

2. The urethral suppository of claim 1 wherein said first end is convex.

3. The urethral suppository of claim 1 wherein said knob is ellipsoidal and has a major axis substantially perpendicular to a longitudinal axis of said shaft.

4. The urethral suppository of claim 1 wherein the therapeutic agent is selected from one or more of the group consisting of antibiotics, antimicrobials, antifungal agents, analgesics, anaesthetics, steroidal anti-inflammatory agents, non-steroidal anti-inflammatory agents, mucous production stimulators, hormones, and anti-spasmodics.

5. The urethral suppository of claim 1 wherein the biocompatible material is a biocompatible carrier medium selected from one or more of the group consisting of modified celluloses, poly(vinyl alcohol), poly (vinylpyrrolidone), polyacrylamide, poly(ethylene glycol), poly (phosphoester urethanes), and ethylenoxide polymers.

6. The urethral suppository of claim 1 wherein the therapeutic agent is disposed throughout the biocompatible material.

7. The urethral suppository of claim 1 wherein the therapeutic agent is applied as a coating to the biocompatible material.

8. The urethral suppository of claim 1 wherein the therapeutic agent is applied differentially to the biocompatible material.

9. The urethral suppository for insertion in a female urethra having a luminal wall, said suppository formed from meltable bicompatible material, said suppository comprising:
    (a) a shaft having a length situated between a first end and a second end; and
    (b) an ellipsoidal knob laterally projecting from the second end of said shaft and sized to prevent insertion of said knob into the urethra,
    wherein said suppository comprises at least one therapeutic agent.

10. A urethral suppository for insertion in a female urethra having a luminal wall, said suppository formed from meltable biocompatible material, said suppository comprising:
    (a) a shaft having a length situated between a first end and a second end; and
    (b) an ellipsoidal knob extending from the second end of said shaft and sized to prevent insertion of said knob into the urethra,
    wherein said suppository comprises at least one therapeutic agent applied as a coating to the biocompatible material.

11. A urethral suppository for insertion in a female urethra having a luminal wall, said suppository formed from meltable biocompatible material, said suppository comprising:
    (a) a shaft having a length situated between a first end and a second end; and
    (b) an ellipsoidal knob extending from the second end of said shaft and sized to prevent insertion of said knob into the urethra,
    wherein said suppository comprises at least one therapeutic agent applied differentially to the biocompatible material.

12. A urethral suppository formed from meltable biocompatible material, said suppository comprising: (a) a shaft having a blunt, rounded first end tapering toward a second end; and (b) an ellipsoidal knob extending from the second end of said shaft and sized to prevent insertion of said knob into the urethra, wherein said shaft and knob comprise at least one therapeutic agent and a meltable biocompatible material.

13. The urethral suppository of claim 12 wherein the therapeutic agent is selected from one or more of the group consisting of antibiotics, anti-microbials, antifungal agents, analgesics, anaesthetics, steroidal anti-inflammatory agents, non-steroidal anti-inflammatory agents, mucous production stimulators, hormones, and anti-spasmodics.

14. The urethral suppository of claim 12 wherein the biocompatible material is a biocompatible carrier medium selected from one or more of the group consisting of modified celluloses, poly(vinyl alcohol), poly (vinylpyrrolidone), polyacrylamide, poly(ethylene glycol), poly (phosphoesterOurethanes), and ethylenoxide polymers.

15. The urethral suppository of claim 12 wherein the therapeutic agent is disposed throughout the biocompatible carrier medium.

16. The urethral suppository of claim 12 wherein the therapeutic agent is applied as a coating to the biocompatible carrier medium.

17. The urethral suppository of claim 12 wherein the therapeutic agent is applied differentially to the biocompatible carrier medium.

18. The urethral suppository of claim 17 wherein said first end is blunt.

19. The urethral suppository of claim 11 wherein said first end is rounded.

20. A method for delivering a therapeutic agent to one or more female structures selected from the group consisting of the urethra, bladder, and periurethral musculature, said the urethra, bladder, and periurethral musculature, said method comprising the step of inserting the suppository of claim 1 into the urethra for a sufficient period of time for said therapeutic agent to diffuse from said suppository to said one or more female structures.

21. A method for delivering a therapeutic agent to one or more female structures selected from the group consisting of method comprising the step of inserting the suppository of claim 12 into the urethra for a sufficient period of time for said therapeutic agent to diffuse from said suppository to said one or more female structures.

\* \* \* \* \*